United States Patent [19]

Bartmann

[11] Patent Number: 5,086,444
[45] Date of Patent: Feb. 4, 1992

[54] PRIMARY RADIATION DIAPHRAGM

[75] Inventor: Guenter Bartmann, Erlangen, Fed. Rep. of Germany

[73] Assignee: Siemens Aktiengesellschaft, Munich, Fed. Rep. of Germany

[21] Appl. No.: 647,980

[22] Filed: Jan. 30, 1991

[30] Foreign Application Priority Data

Feb. 16, 1990 [EP] European Pat. Off. ........ 90103049.4

[51] Int. Cl.$^5$ .............................................. G21K 1/04
[52] U.S. Cl. ..................................... 378/152; 378/150
[58] Field of Search ................ 378/152, 150, 151, 153

[56] References Cited

U.S. PATENT DOCUMENTS

| | | | |
|---|---|---|---|
| 3,115,580 | 12/1963 | Brewer | 378/152 |
| 4,672,652 | 6/1987 | Huttenrauch et al. | 378/152 |
| 4,794,629 | 12/1988 | Pastyr et al. | 378/152 |
| 4,897,861 | 1/1990 | Schaefer et al. | |

FOREIGN PATENT DOCUMENTS 2053089  5/1972  Fed. Rep. of Germany .

*Primary Examiner*—Craig E. Church

[57] ABSTRACT

A primary radiation diaphragm for use in a medical radiation application apparatus for gating the x-ray beam emitted by a radiation source onto a desired region has first and second diaphragm plates and an actuator for the diaphragm plates having two ranges of adjustment. The first diaphragm plate is adjusted within the first range of adjustment by movement of the actuator, and the second diaphragm rate is adjusted by moving the actuator within the second range of adjustment.

8 Claims, 4 Drawing Sheets

PRIMARY RADIATION DIAPHRAGM

BACKGROUND OF THE INVENTION

1. Field of the Invention

The present invention is directed to a primary radiation diaphragm of the type used in a medical radiation application apparatus.

2. Description of the Prior Art

A primary radiation diaphragm is used in a medical radiation application apparatus to gate the x-ray beam emitted by a radiation source onto a desired region of a patient.

A primary radiation diaphragm as disclosed in German OS 20 53 089 having a plurality of diaphragm lamellae which are radially adjustable. These diaphragm lamellae are seated on a carrier plate which is disposed in a plane perpendicular to the central ray of the radiation beam. For adjusting the diaphragm lamellae, tangential guide channels are provided in the carrier plate and radial guide channels are provided in a set collar. The diaphragm plates have pins which engage these channels. When the set collar, which is seated on driven guide rollers, is rotated around its central axis relative to the carrier plate, the diaphragm lamellae are tangentially displaced, as a result of which the diaphragm aperture either enlarges or diminishes in size, dependent on the rotational direction of the collar.

Another primary radiation diaphragm is disclosed in European application 0 304 773 corresponding to U.S. Pat. No. 4,897,861, for an x-ray diagnostic apparatus, wherein two diaphragm plates are adjustable in plane perpendicular to the central ray of the x-ray beam. For gating the useful portion of the x-ray beam, the diaphragm plates, by appropriate adjustment, can form a slot or a V-shaped opening, with the slot or V-shaped opening lying either centrally or eccentrically relative to the central ray. The diaphragm plates are seated on a rotatable ring and have oblong holes into which pins of levers extend. The pins are displaceable within the oblong holes. The levers are seated so as to be rotatable around respective axes using an electric motor, so that the levers are pivoted, and thus the diaphragm plates are adjusted when the electric motors are driven. Because each lever is individually pivotable, the diaphragm plates can be adjusted not only radially relative to the central ray, but also obliquely relative to the central ray. The axes have potentiometers allocated to them which supply electrical signals corresponding to the positions of the levers, and thus corresponding to the adjustment of the diaphragm plates. These electrical signals are supplied to a control unit for the primary radiation diaphragm for processing.

SUMMARY OF THE INVENTION

It is an object of the present invention to provide a primary radiation diaphragm for a medical radiation application apparatus which has a space-saving structure and which is simple and economic to manufacture.

The above object is achieved in accordance with the principles of the present invention in a primary radiation diaphragm having first and second diaphragm plates and an actuator having two ranges of adjustment which is used to adjust the positions of the first and second diaphragm plates. The first diaphragm plate is adjusted by movement of the actuator within the first range of adjustment and the second diaphragm plate is adjusted by movement of the actuator within the second range of adjustment.

An advantage of the primary radiation diaphragm disclosed herein is that only one actuator having two ranges of adjustment is required for adjusting both the first and second diaphragm plates, so that the apparatus requires little outlay in terms of structural components, and the spatial dimensions of the radiation diaphragm are maintained compact.

An especially compact structure of the primary radiation diaphragm is achieved in an embodiment wherein the actuator is formed by a first control disc, disposed opposite a first side of a carrier disc for the diaphragm plates, and a second control disc disposed opposite a second side of the carrier disc, the carrier disc and the first and second control discs being adjustable around a common, central axis. Two oppositely adjustable diaphragm plates are respectively adjustable by the first control disc at one side of the carrier disc, and first and second diaphragm plates are also disposed on the other side of the carrier plate which are adjustable by the first and second control discs. An especially compact structure is obtained in this manner, with the two different diaphragms of the primary radiation diaphragm being adjustable for gating the radiation beam.

DESCRIPTION OF THE PREFERRED EMBODIMENTS

Figure 1:
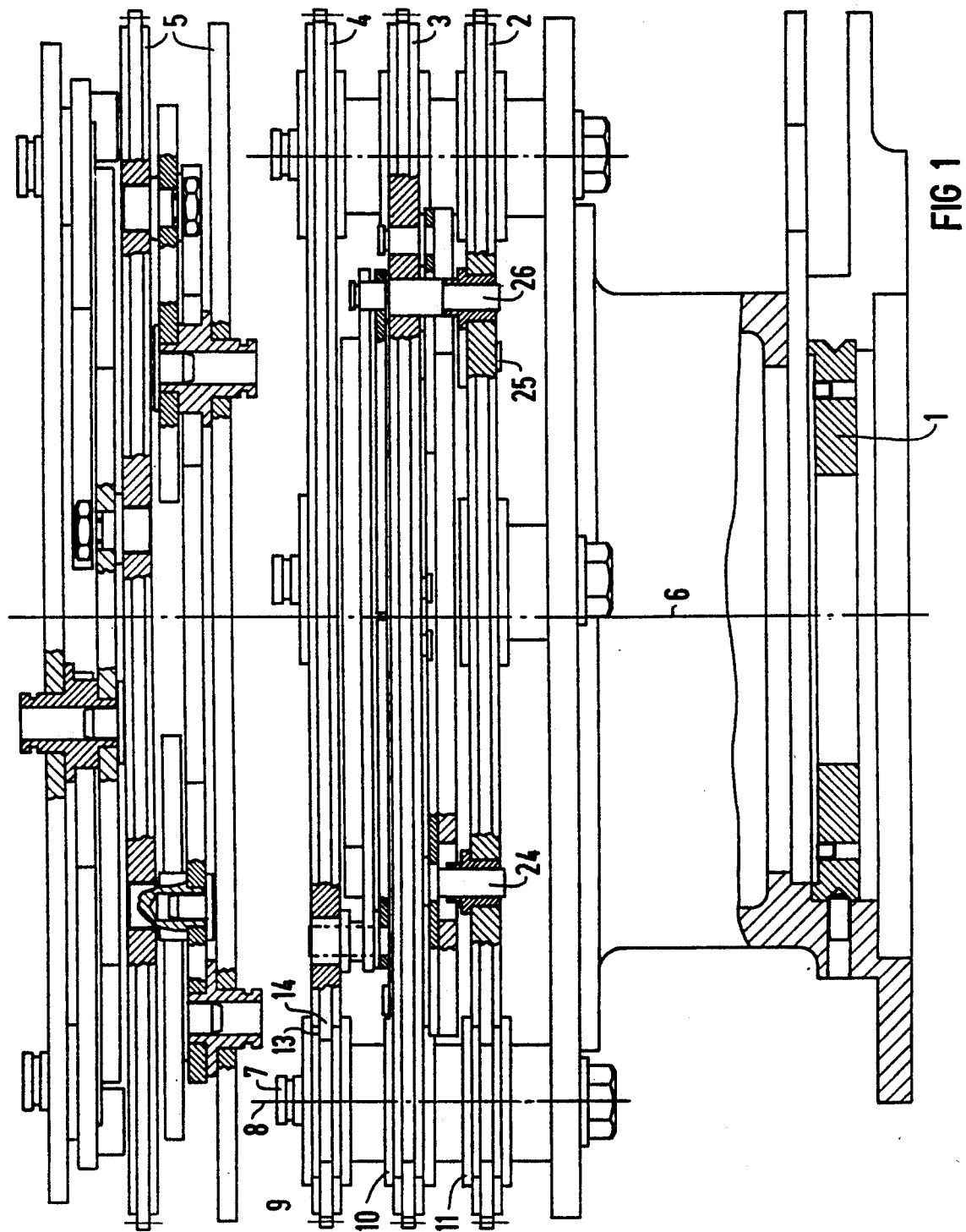
FIG. 1 is a side view, partly in section, of a primary radiation diaphragm constructed in accordance with the principles of the present invention.

A primary radiation diaphragm constructed in accordance with the principles of the present invention is shown in FIG. 1. The diaphragm includes a focus-proximate iris diaphragm 1, a first control disc 2 arranged above the focus-proximate iris diaphragm 1 and functioning as an actuator, a carrier disc 3 for diaphragm plates disposed above the first control disc 2, a second control disc 4 disposed above the carrier disc 3 and functioning as an actuator, and a focus-distal iris diaphragm 5 disposed above the second control disc 4. The arrangement has a central axis 6 which is coincident with the central beam of the useful radiation beam of a radiation source, for example, an x-ray source.

The iris diaphragms 1 and 5, which are not shown in greater detail, each consist of eight rotatably seated tantalum or lead lamellae arranged staggered in four planes of two lamellae each. The iris diaphragms 1 and 5 are respectively set to the desired gating diameter by a control disc. The control discs of the iris diaphragms 1 and 5 are matched to each other so that the gating of the focus-proximate iris diaphragm 1 is always slightly larger than the gating of the focus-distal iris diaphragm 5. The control discs of the iris diaphragms 1 and 5 are driven by an electric motor, with signals identifying the size of the respective openings of the diaphragms 1 and 5 being acquired by an optoelectrical position generator.

Three bearings are provided for the first and second control discs 2 and 4 and the carrier disc 3. The structure of each bearing is the same, and is shown with respect to the bearing identified with reference number 7. The bearing 7 has a central axis 8 on which cylindrical bearing elements 9, 10 and 11 are arranged at a spacing from each other. The cylindrical bearings 9, 10 and 11 are rotatable around the central axis 8. The cylindrical bearing elements 9, 10 and 11 are identical, and as shown for the cylindrical bearing element 9, have a channel 13 for, for example, accepting the edge region 14 of the second control disc 4. The channel of the cylindrical bearing element 10 accepts the edge region of the carrier disc 3 and the channel for the cylindrical bearing element 11 accepts the edge region of the first control disc 2. The first and second control discs 2 and 4 and the carrier disc 3 are thus held at a distance relative to each other by the three bearings 7, and are rotatable around the central axis 6. An electromotive drive is provided for the first and second control discs 2 and 4 as well as for the carrier disc 3, so that these can be offset by an angular amount relative to each other, and can be adjusted with the same or opposite rotational directions around the axis 6.

A position generator, with which the respective position and rotational direction can be acquired, is provided for each of the first and second control discs 2 and 4 and the carrier disc 3. This may ensue, for example, by means of a line marking on each disc and an optoelectronic transmitter/receiver.

Figure 2:
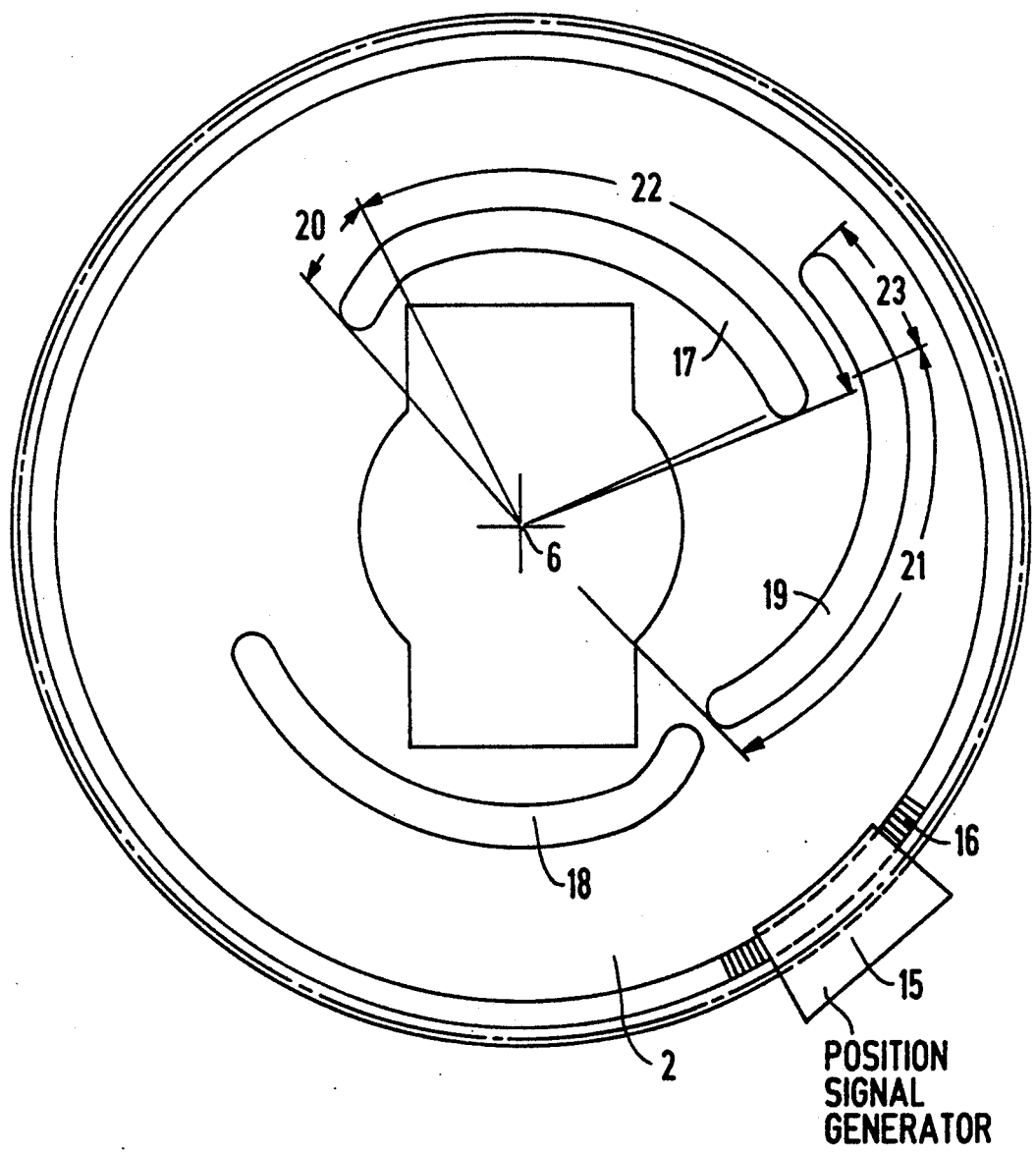
FIG. 2 is a plan view of control disc for the primary radiation diaphragm of FIG. 1.

FIG. 2 shows the first control disc 2 and a position generator 15. Markings 16 are applied at the edge region of the control disc 2 with which the starting point, the amount of movement around the central axis 6, and the rotational direction can be acquired by means of the position generator 15. The control disc 2 has three radial cams 17, 18 and 19, with the radial cam being disposed on the control disc 2 identical to the radial cam 17, but offset by 180°. As shown with respect to the cam 17, the cams 17 and 18 have a first region 20 which corresponds to the region 21 of the radial cam 19, wherein the spacing to the central axis 6 varies. The spacing with respect to the central axis 6 is constant in a region 22 of the radial cams 17 and 18, which corresponds to a region 23 of the radial cam 19. As shown in FIG. 1, control pins 24 and 25 of the diaphragm plates of a fixed diaphragm, arranged at a first side of the carrier disc 3 engage the radial cams 17 and 18. As also shown in FIG. 1, a control pin 26 of a diaphragm plate of a slotted diaphragm arranged at a second side of the carrier disc 3 engages the radial cam 19.

Figure 3:
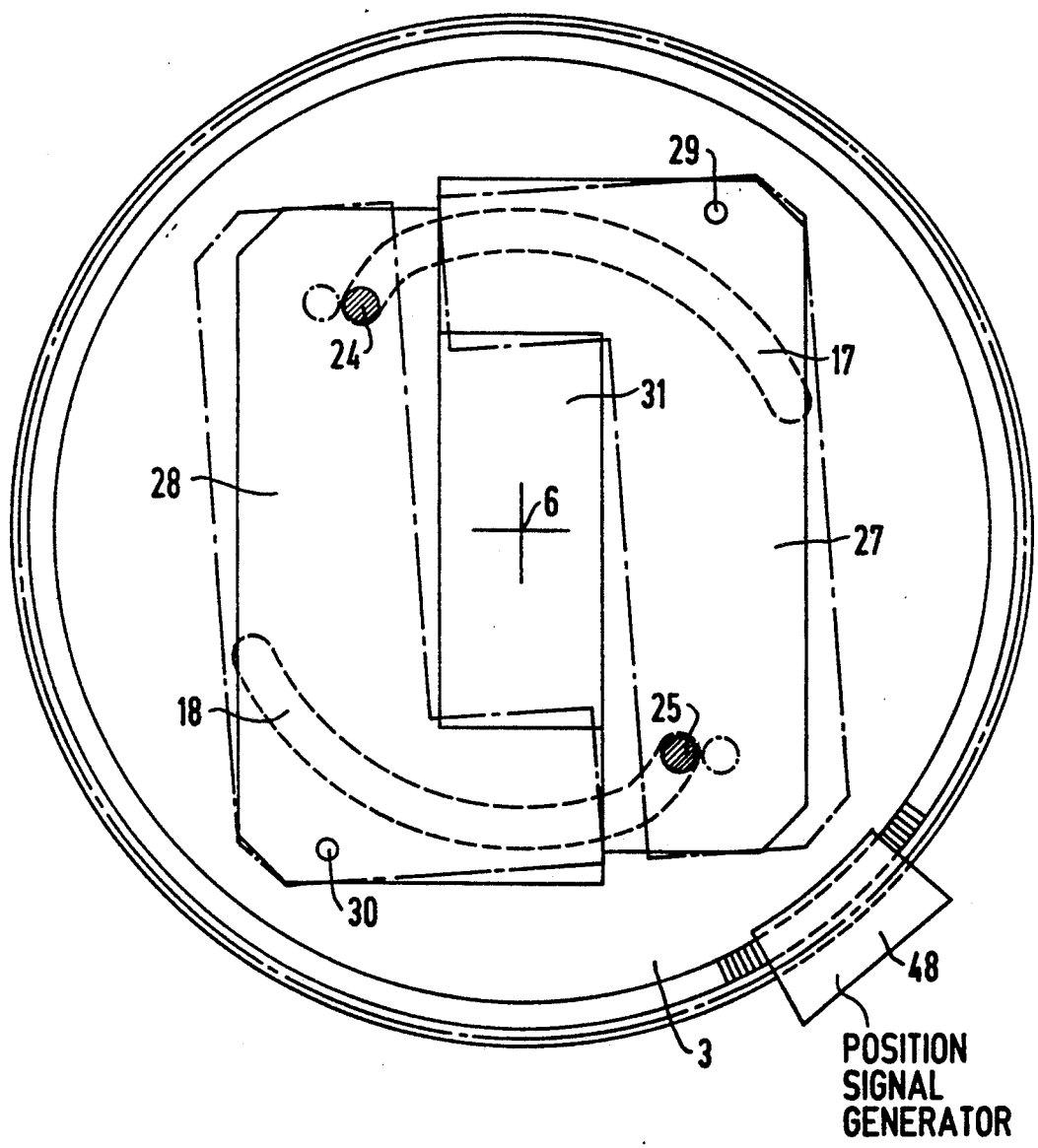
FIG. 3 is a plan view of a side of the carrier plate for the diaphragm plates of the primary radiation diaphragm of FIG. 1.

The first side of the carrier disc 3 is shown in a plan view in FIG. 3, i.e., as seen by the focus-proximate iris diaphragm 1. Elements which have already been provided with reference numerals have the same reference numerals in FIG. 3. The radial cams 17 and 18 of the first control disc 2 are shown with dashed lines, however, they are not elements of the carrier disc 3. A diaphragm plate 27 is mounted rotatable around an axis 29 at the first side of the carrier disc 3, and a further diaphragm plate 28 of the fixed diaphragm is mounted rotatable around an axis 30 at the first side of the carrier disc 3. The diaphragm plates 27 and 28 are L-shaped, and are offset by 180° relative to each other.

In a first position, the respective short legs of the diaphragm plates 27 and 28 lie against the respective long leg of the other diaphragm plate, so that two diaphragm plates 27 and 28 bound a rectangular region 31.

In this first position, for example, the x-ray beam can be gated onto a rectangular x-ray receiver, for example onto x-ray film. The control pins 24 and 25 discussed in connection with FIG. 2 are situated at the left in this first position, i.e., at the start of the range 20 of the radial cams 17 and 18. When, given a stationary carrier disc 3, the control disc 2 is rotated counter-clockwise, or given a stationary control disc 2, the carrier disc 3 is rotated clockwise, the control pins 24 and 25 are guided in the region 22 of the radial cams 17 and 18, i.e., in the outward direction. The diaphragm plates 27 and 28 are thereby pivoted around the axes 29 and 30, so that the short legs of the diaphragm plates 27 and 28 are no longer in contact with the long legs of the other diaphragm plate, and the long legs of the diaphragm plates 27 and 28 assume a larger distance from each other.

When the control pins 24 and 25 are situated in the region 22 (FIG. 2), no further adjustment of the diaphragm plates 27 and 28 ensues, because the region 22 has a constant spacing relative to central axis 6. The diaphragm plates 27 and 28 thus assume a second position. In this second position, the spacing of the long legs of the diaphragm plates 27 and 28 is selected so that the x-ray beam at least illuminates a nine inch input luminescent screen of an x-ray image intensifier. The gating of the x-ray beam to a seven inch or to a nine inch input luminescent screen can then be undertaken using an iris diaphragm.

If, in the first or second position of the diaphragm plates 27 and 28, the carrier disc and the control disc 2 are rotated in common around the central axis, the region 31 is also rotated around the central axis 6.

Figure 4:
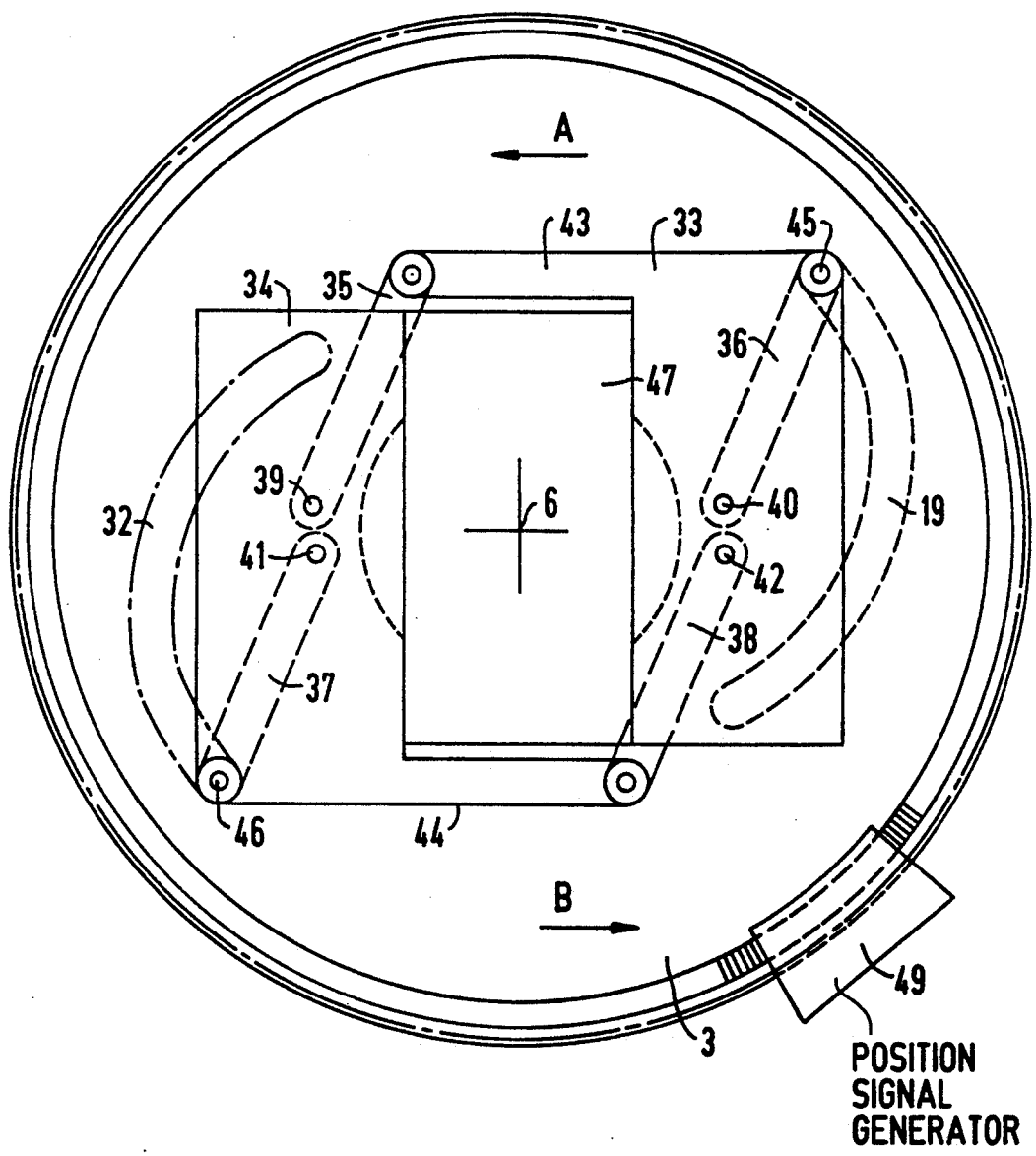
FIG. 4 is a plan view of the opposite side of the carrier plate of the primary radiation diaphragm of FIG. 1.

The second side of the carrier disc 3 is shown in FIG. 4, as seen from the focus-distal iris diaphragm 5. The radial cam 19 of the control disc 2 is shown with dashed lines. A further radial cam 32 in the second control disc 4 is shown with dot-dashed lines. In this figure, the second control disc 4 is shown as if it were transparent over the second side of the carrier disc 3. Two diaphragm plates 33 and 34 of the slotted diaphragm are adjustable at the second side of the carrier disc 3. The diaphragm plate 33 is held by two linking arms 35 and 36, and the diaphragm plate 34 is held by two linking arms 37 and 38. One end of each of the linking arms 35, 36, 37 and 38 is connected to carrier disc 3 by a respective one of shafts 39, 40, 41 and 42. The respective opposite ends of each pair of linking arms are connected to the diaphragm plates 33 or 34. A parallelogram arrangement is thus formed with which the diaphragm plates 33 and 34 can be adjusted parallel to each other at the second side of the carrier disc 3. For adjusting the diaphragm plates 33 and 34, a control pin 45 of the diaphragm plate 33 engages through the carrier disc 3 into the radial cam 19 of the first control disc 2, and a control pin 46 for the diaphragm plate 34 engages into the radial cam 32 of the second control disc 4, arranged over the carrier disc 3.

As shown in FIG. 2 with reference to the example of the radial cam 19, the radial cams 19 and 32 have a first region 23 wherein the distance from the central axis 6 is constant, and have a second region 21 wherein the distance from the central axis 6 changes. When the first control disc 2 is turned counter-clockwise around the axis 6, the control pin 45 is guided in the radial cam 19 out of the region 23 into the region 21, causing the diaphragm plate 33 to be adjusted toward the left, i.e., in the direction referenced A. Analogously, the diaphragm plate 34 is also adjusted when the second control disc 4 is rotated counter-clockwise around the axis 6, given a stationary carrier disc 3. The diaphragm plate 34, however, is caused to move in the direction referenced B. Dependent on the rotational direction of the first and second control discs 2 and 4, the diaphragm plates 33 and 34 of the slotted diaphragm can be individually adjusted. The region 47 gated by the diaphragm plates 33 and 34 can be rotated around the central axis 6 by rotating the first and second control discs 2 and 4 and the carrier disc 3 around the central axis 6 in the same direction and with the same rotational speed.

The position of the diaphragm plate 33 is acquired by a position generator 48 of the carrier disc 3, and the position generator 15 of the first control disc 2, and the position of the diaphragm plate 34 is acquired by a position generator 48 of the carrier disc 3 and a position generator 49 of the second control disc 4.

The diaphragm plates 33 and 34 can also be adjusted by rotating the carrier disc 3 around the central axis 6 and maintaining the first and second control discs 2 and 4 stationary.

Given the adjustment of the first control disc 2 as an actuator around the central axis 6 in a first range of adjustment corresponding to the region 20, the diaphragm plates 27 and 28 will be adjusted, and given further movement of the first control disc 2 in a second range of adjustment, corresponding to the region 21, the diaphragm plate 33 is adjusted. It is thus possible to adjust two diaphragm plates on the basis of one control disc, so that an extremely compact structure of the primary radiation diaphragm results. The manufacturing costs are reduced because an additional control disc, and the bearings, drive elements and position generators associated therewith, are not needed for adjustment of the diaphragm plate 33. If the control discs 2 and 4 and the carrier disc 3 are composed of a material relatively impermeable to radiation, they will preferably have a central opening which is matched to the desired, largest aperture of the useful radiation beam.

Although modifications and changes may be suggested by those skilled in the art, it is the intention of the inventor to embody within the patent warranted hereon all changes and modifications as reasonably and properly come within the scope of his contribution to the art.

I claim as my invention:

1. A primary radiation diaphragm for a medical radiation application apparatus, said primary radiation diaphragm comprising:

first and second diaphragm plates; and
actuator means in mechanical connection with said first and second diaphragm plates and having first and second different ranges of adjustment for respectively differently adjusting said first and second diaphragm plates in succession with said first diaphragm plate being adjusted by initially moving said actuator means within said first range of adjustment and said second diaphragm plate being adjusted by subsequently moving said actuator means within said second range of adjustment, wherein said actuator means is a control disc rotatable around a central axis through said first and second ranges of adjustment in succession so that as said control disc is rotated around said central axis said first diaphragm plate is adjusted in said first range of adjustment and as said control disc is further rotated around said central axis the position of said first diaphragm plate remains constant and said second diaphragm plate is adjusted in said second range of adjustment.

2. A primary radiation diaphragm as claimed in claim 1 wherein said actuator and said first diaphragm plate are mechanically connected so that said first diaphragm plate assumes a first extreme position at a start of said first region of said actuator and assumes a second extreme position at an end of said first region of said actuator.

3. A primary radiation diaphragm as claimed in claim 1 further comprising a carrier disc and wherein said first diaphragm plate is disposed on a first side of said carrier disc and said second diaphragm plate is disposed on a second, opposite side of said carrier disc.

4. A primary radiation diaphragm as claimed in claim 3 wherein said control disc is disposed on said first side of said carrier disc and wherein said actuator means includes a further control disc disposed at said second side of said carrier disc, means for adjusting said carrier disc and said control disc and said further control disc around said central axis, with two diaphragm plates, one of which is said first diaphragm plate, being oppositely adjustable by said first control disc at said first side of said carrier disc and second diaphragm plate being disposed at said second side of said carrier plate adjustable by said control disc, and further comprising a further diaphragm plate adjustable by said further control disc disposed at said second side of said carrier disc.

5. A primary radiation diaphragm as claimed in claim 4 further comprising means for selectively individually or in common rotating said control disc, said further control disc and said carrier discs around said central axis.

6. A primary radiation diaphragm as claimed in claim 5 further comprising a plurality of position generators respectively associated with each of said control disc, said further control disc and said carrier disc.

7. A primary radiation diaphragm as claimed in claim 6 wherein said position generator includes means for generating the position and rotational direction of the associated disc.

8. A primary radiation diaphragm as claimed in claim 3 further comprising an iris diaphragm disposed at the side of said control disc facing away from said carrier disc.

* * * * *